(12) United States Patent
Chewins (10) Patent No.: US 7,967,800 B2
(45) Date of Patent: Jun. 28, 2011

(54) APPARATUS AND METHODS FOR DISINFECTING A SURFACE

(75) Inventor: John George Chewins, Andover (GB)

(73) Assignee: Bioquell UK Limited (GB)

( * ) Notice: Subject to any disclaimer, the term of this patent is extended or adjusted under 35 U.S.C. 154(b) by 329 days.

(21) Appl. No.: 10/557,862

(22) PCT Filed: May 24, 2004

(86) PCT No.: PCT/GB2004/002212
§ 371 (c)(1), (2), (4) Date: Sep. 12, 2006

(87) PCT Pub. No.: WO2004/103452
PCT Pub. Date: Dec. 2, 2004

(65) Prior Publication Data
US 2007/0163935 A1    Jul. 19, 2007

(30) Foreign Application Priority Data
May 23, 2003 (GB) .................................. 0311958.3

(51) Int. Cl.
*A61M 35/00* (2006.01)
(52) U.S. Cl. .......... 604/289; 604/25; 604/290; 604/293; 210/760; 210/765; 128/202.25
(58) Field of Classification Search ............... 604/25, 604/289, 290, 293
See application file for complete search history.

(56) References Cited

U.S. PATENT DOCUMENTS

| | | | | |
|---|---|---|---|---|
| 3,739,983 A | * | 6/1973 | Jousson | 239/101 |
| 4,375,812 A | | 3/1983 | Vaseen et al. | |
| 4,422,450 A | * | 12/1983 | Rusteberg | 601/162 |
| 5,098,415 A | | 3/1992 | Levin | |
| 5,423,902 A | * | 6/1995 | Strutz et al. | 95/273 |
| 5,636,643 A | * | 6/1997 | Argenta et al. | 128/897 |
| 5,664,593 A | * | 9/1997 | McClain | 132/333 |
| 5,683,576 A | * | 11/1997 | Olsen | 210/138 |
| 5,834,031 A | | 11/1998 | Martin et al. | |

(Continued)

FOREIGN PATENT DOCUMENTS

FR    2 784 388 A1    4/2000

(Continued)

OTHER PUBLICATIONS

George D. Winter, *Formation of the Scab and the Rate of Epithelization of Superficial Wounds in the Skin of the Young Domestic Pig*, Nature, vol. 193, No. 4812, Jan. 20, 1962, pp. 293-294.

(Continued)

*Primary Examiner* — Michele Kidwell
*Assistant Examiner* — Ilya Y Treyger
(74) *Attorney, Agent, or Firm* — Workman Nydegger (57) ABSTRACT

An apparatus for disinfecting surfaces and in particular human and animal wounds, includes a contractor for accumulating concentrated ozonated water and systems to deliver ozonated water from the reservoir to a nozzle having one or more jets for delivering a spray of ozonated water on to the surface to be treated. The nozzle has an encircling shroud and systems are provided for withdrawing ozonated gas liberated at the nozzle from around the nozzle. A collection tray is provided which is located under the surface/wound to be treated to receive ozonated water flowing from the treatment region and where any residual ozone is broken down.

31 Claims, 9 Drawing Sheets

U.S. PATENT DOCUMENTS

| | | | |
|---|---|---|---|
| 5,839,155 A | 11/1998 | Berglund et al. | |
| 6,073,627 A | 6/2000 | Sunnen | |
| 6,142,982 A * | 11/2000 | Hunt et al. | 604/313 |
| 6,455,017 B1 | 9/2002 | Kasting, Jr. et al. | |
| 6,503,403 B2 * | 1/2003 | Green et al. | 210/748 |
| 2002/0139755 A1 | 10/2002 | Green et al. | |

FOREIGN PATENT DOCUMENTS

| | | | |
|---|---|---|---|
| GB | 546646 | | 6/1941 |
| GB | 546646 | * | 7/1942 |
| GB | 2125296 | * | 8/1982 |
| GB | 2125296 A | * | 3/1984 |
| GB | 2125296 | * | 8/1984 |
| JP | 03-169341 | | 7/1991 |
| JP | 06-064904 | | 3/1994 |
| JP | 06-233805 | | 8/1994 |
| RU | 2 175 539 C2 | | 3/1999 |
| RU | 2 178 699 C1 | | 1/2002 |
| WO | WO 00/20343 | | 4/2000 |
| WO | WO 01/72432 A1 | | 10/2001 |
| WO | WO 01/93793 A1 | | 12/2001 |

OTHER PUBLICATIONS

D.J. Baker, *Severe Trauma Infections,* Anesthesia, vol. 53, (Suppl. 2), 1998, pp. 65-67.

Thomas K. Hunt, MD, *Wound Healings and Wound Infection, What Surgeons and Anesthesiologists Can Do,* Wound Healing, vol. 77, No. 3, Jun. 1997, pp. 587-606.

John U. Bascom, *Pilonidal Care: Anaerobes as Invisible Villains,* Letter to the Editor, 1997 Scandinavian University Press.

P.G. Bowler et al., *Wound Microbiology and Associated Approaches to Wound Management,* Clinical Microbiology Review, vol. 14, No. 2, Apr. 2001, pp. 244-269.

Chandan K. Sen et al., *Oxidant-Induced Vascular Endothelial Growth Factor Expression in Human Keratinocytes and Cutaneous Wound Healing,* The Journal of Biological Chemistry, vol. 277, No. 36, Sep. 6, 2002, pp. 33284-33290.

Robert Greif, MD, *Supplemental Perioperative Oxygen to Reduce the Incidence of Surgical-wound Infection,* The New England Journal of Medicine, Vo. 342, No. 3, Dec. 6, 2005, pp. 161-167.

N.J. Trengove, *Qualitative Bacteriology and Leg Ulcer Healing,* Journal of Wound Care, vol. 5, No. 6, Jun. 1996, pp. 277-280.

Mater Misericordiae University Hospital Ltd., *Facing the Challenge of Wound Management in the 21st Century,* Freeman Auditorium, Oct. 10, 2002, 9 pages.

* cited by examiner

APPARATUS AND METHODS FOR DISINFECTING A SURFACE

BACKGROUND OF THE INVENTION

1. Field of the Invention

This invention relates to apparatus and methods for use in the disinfection of surfaces and in particular to disinfect wounds using a high concentration aqueous ozone and also to methods and apparatus for producing a high concentration aqueous solution of ozone.

2. Present State of the Art

Wounds can be divided into two basic categories, acute and chronic. Acute wounds are caused when damage occurs to external intact skin tissue. This includes surgical wounds, bites, burns, cuts, abrasions, lacerations and more traumatic crush or gunshot wounds. Chronic wounds are associated with endogenous mechanisms connected to a predisposed condition that eventually damages the dermal tissue. Chronic wounds often result when the supply of oxygen and nutrients (perfusion) to tissues is impaired. Reduced arterial supply, venous drainage or metabolic diseases can cause chronic wounds. Leg ulcers, foot ulcers and pressure sores are all examples of chronic wounds.

Hunt et al (Hunt, T. K. and Hopt, H. W. 1997, Wound healing and infection—what surgeons and anaesthesiologists can do. Surg. Clin. North America. Vol 77, p 587-606) state that acute wounds will heal rapidly if blood perfusion is maximised, thus providing the cells of the immune system the oxygen and nutrients necessary to ward off infection. Oxygen is an integral requirement for cell growth, division and wound healing Grief et al (Grief R., Akca, O., Horn, E., Kurz, A., and Sessler, D. J. 2000. Supplemental perioperative oxygen to reduce the incidence of surgical wound infection. The New England Journal of Medicine. Vol 342, p 161-167). It is also critical for the respiratory burst of Polymorphonuclear leukocytes (PMNs), which produce potent anti-microbial compounds. As well as providing the energy for metabolic reactions and hence infection defence mechanisms, oxygen also plays a major role in determining the oxidation—reduction potential of tissues. Bakker (Bakker, D. J. 1998. Severe trauma and infections. Anaesthesia. Vol 53, p 65-67). Wound microbiology and associated approaches) identifies that a low redox potential favours the growth of anaerobic bacteria. Bowler et al (Bowler, P. G. Duerden, D. I., and Armstrong, D. G. 2001. Wound microbiology and associated approaches to wound management. Clinical Microbiology Reviews. Vol 14, No 2, p 244-269) state that a low redox potential will facilitate the development of synergistic aerobic/anaerobic populations.

Wounds often have a diverse array of microflora. The primary pathogens involved in the infection of chronic and acute wounds are thought to be *Staphylococcus aureus, Pseudomonas aeruginosa* and beta-hemolytic streptococci. These pathogens are aerobic or facultative. However, anaerobic pathogens are often overlooked in wound infection investigations, because they reside deep within the dermal tissue. Anaerobic micro-organism isolation, identification and collection are time consuming and labour intensive. Bowler et al (referred to above) investigated and conclude that there is correlation between the incidence of anaerobic pathogens and the prevalence of infection. Bascom (Bascom, J. U. 1996. Pilonidal care: anerobes as visible villans. European Journal of Surgery. Vol 162, p 351) reports that anaerobic bacteria are the true causative micro-organisms of wound infection and that improved oxygenation of wounds is required to minimise infection.

The polymicrobial nature of wounds has been widely published, however *Staphylococcus aureus* is considered to be the most problematic bacterium in traumatic, surgical and burn wound infections Bowler et al (referred to above), Tengrove et al (Tengrove, N. J., Stacey, M. C. McGechie, D. F. and Mata, S. 1996. Qualitative bacteriology and leg ulcer healing. Journal of wound care. Vol 5, p 277-280) report that when four or more bacterial groups are present within a leg ulcer, the likelihood of healing is significantly reduced. This finding promotes the hypothesis that microbial synergy occurs within wounds increasing the net pathogenic effect and severity of the infection. Oxygen consumption by aerobic bacteria induces tissue hypoxia and lowers the redox potential, which provides a more favourable habitat for anaerobic organisms. Nutrients produced by one micro-organism may encourage the growth of potentially pathogenic co-habiting micro-organisms. Some anaerobes are able to impair host immune cell function and hence provide an advantage for themselves and other co-habiting micro-organisms. Bowler (Bowler, P. G. 2002. Microbiology of acute and chronic wounds. Facing the challenge of wound management in the 21st Century. Master Misericordiae University Hospital) states that micro-organisms are able to aid each other within a wound. Micro-organisms (especially in biofilms) use a communication mechanism called Quorum sensing. This is a cell density dependent form of communication, facilitating survival in a new harsh environment. They release signalling molecules informing each other of "survival tips" (i.e. produce a specific morphological change or a specific defensive chemical).

Debridement is an integral part of wound healing. The removal of dead and unhealthy tissue is essential to minimise the habitat available for microbial colonisation and allow new tissue formation. Debridement is achieved through physical removal of tissue using a sharp instrument or the application of saline or sterile water. The management of bite wounds involves high pressure irrigation to reduce microbial load.

Historically ozone has been used to disinfect wounds in its gaseous form or dissolved within oil. Direct ozone gas application, intravenous injection, rectal insufflation or autohemoozonotherapy are all known methods of medical ozone application. Reference should be made to the following Patent Publications for details of such treatments: RU-2178699, FR-2784388, U.S. Pat. No. 6,073,627.

Aqueous Ozone Hypotheses

1. Disinfection 1.1. Ozone is highly reactive and decomposes through the formation of free radicals to form molecular oxygen. Free radicals have an unpaired electron in their outer orbital making them highly unstable and reactive. These free radicals comprise hydroxyl, superoxide or ozonide radicals. Ozone micro-organism attack is primarily on the cellular membrane, with damage subsequently occurring to other cell sites. The proposed mechanism of action is thought, in large part, to relate to the olefinic bonds within the micro-organism cell membrane being attacked by ozone to form an ozonide or other decomposition product. The ozonide reacts with enzymes, sulfhydryl groups and aldehydes, releasing peroxyl compounds. The peroxyl compounds further damage proteins, DNA and other structures. The cell is lysed and the cytoplasm dispersed. In essence, the aqueous ozone would be used to reduce the microbiological organisms within the wound.

1.2. Aqueous ozone will be particularly effective against anaerobic bacteria due to their lack of anti-oxidants and other oxidation defence systems. Aerobic bacteria produce anti-oxidants such as superoxide dismutase to prevent cellular damage caused through respiration using oxygen. Anaerobic bacteria do not use oxygen to respire and hence have not evolved advanced anti-oxidants. The removal of anaerobic bacteria will reduce the likelihood of infection Bowler (referred to above).

1.3. Free radical based oxidation is random and hence it will be extremely difficult for a micro-organism to develop resistance to aqueous ozone. Free radical based disinfection does not involve target site specificity. Free radicals will be effective against all micro-organisms, with the killing rate being dependent on, among other things, the prevalence of anti-oxidants within different microbial species.

1.4. A sufficiently long contact period will remove all micro-organisms from a wound bed, creating a sterile environment.

2. Debridement 2.1. Aqueous ozone is not cell specific and will attack the wound tissue as well as the micro-organisms. Unhealthy or dead tissue is less well perfused than healthy tissue and as such does not contain as much anti-oxidant or enzymatic agents (superoxide, dismutase, glutathione, macrophage, etc). The unhealthy tissues will mount a far weaker defence against the free radical attack than the healthy tissues and hence will be more prone to damage/rupture/removal than healthy tissues. Hence, the aqueous ozone will provide a quasi-selective chemical debridement system, creating an improved healing environment.

3. Moist Healing Environment 3.1. The application of aqueous ozone will provide a moist healing environment (in conjunction with 1.4.). A moist healing environment is critical to wound healing Winter (Winter, G. D. 1962. Formation of scab and the rate of epithelization of superficial wounds in the skin. Nature. Vol 193, p 293-294).

4. Reactive Oxygen Species (ROS)

4.1. Aqueous ozone produces Reactive Oxygen Species (ROS) as decomposition intermediaries. The ROS produced will complement the bodies own natural defence system in which polymorphonucleocytes (PMNs) produce ROS to remove micro-organisms. The aqueous ozone healing system is biomimetic, providing a "booster" when the bodies own PMNs have been overwhelmed by infection.

4.2. Aqueous ozone will act as an ROS generator in poorly perfused ischemic tissues. The lack of perfusion inhibits the body's own production of ROS through a deficiency in nutrient/oxygen/energy. The aqueous ozone artificially creates the body's natural infection removal mechanism.

4.3. ROS will support the formation of blood vessels (angiogenesis) and stimulate collagen production (Sen, C. K., Khanna, S., Babiar, B. M., Hunt, T. K., Ellison, E. C., and Roy, S. 2002. Redox control of wound repair. JCB (paper in press) Manuscript M203391200).

4.4. Micro-organisms communicate through quorum sensing, which is facilitated through the release of signalling molecules. ROS may actively oxidise these signalling molecules reducing synergistic survival effects. This mechanism would be important in reducing any biofilm formation.

5. Oxygenation 5.1. Aqueous ozone decomposes to water and oxygen. The decomposition reaction takes place within the wound providing surface application of oxygen to cells and produces a hyperoxic environment. Anaerobic bacteria cannot survive in a hyperoxic environment, reducing infection.

5.2. A hyperoxic environment produced through aqueous ozone application can provide a source of oxygen to poorly perfused tissues (ischemic), which may improve wound healing.

5.3. Cytokines and growth factors show an improved mechanistic action in a hyperoxic environment, which can be facilitated through the use of aqueous ozone application equipment.

5.4. The aqueous ozone application equipment contains an oxygen concentrator that can be used to provide high pressure sterile oxygen to a wound. Oxygen is critical to the wound healing process. The equipment allows the application of oxygen to the wound via a high pressure jet or through the use of a hyperbaric chamber around the wound area.

6. Acute Wound Response 6.1. Research has identified that inflicting an acute wound within a chronic wound can induce a wound healing response. The cellular oxidation caused by aqueous ozone application may induce an acute wound type response within a non-healing chronic wound.

Ozonated Water

Ozonated water is widely used to kill bacteria and other micro-organisms. However, when generating and dissolving ozone in water it is usual to expect levels of under 1 ppm.

WO-A-0020343 discloses an apparatus for producing an aqueous ozone solution to disinfect animal house feed water. The process requires pressurisation of the contactor to facilitate ozonation.

U.S. Pat. No. 5,834,031 discloses an apparatus that utilises aqueous ozone to treat foot fungi. A single "in-line" ozonation process is used to produce aqueous ozone, whilst completely submerging the appendage to be treated.

U.S. Pat. No. 5,098,415 discloses an apparatus to treat foot diseases using aqueous ozone utilising submersion of the appendage into aqueous ozone solution.

WO-A-0172432 discloses a mobile spray apparatus for providing an aqueous ozone stream. The aqueous ozone production process uses an "in-line" method of production as well as a de-gas unit.

U.S. Pat. No. 6,455,017 discloses a mobile apparatus for washdown and sanitising using aqueous ozone. The aqueous ozone production process uses an "in-line" method of production.

US-A-2002139755 discloses a method for enhancing dissolution of gasses in liquids. The method uses a plurality of nozzles sized and sited to produce micro-fine bubbles and initiate rotational flow.

RU-A-2175539 discloses a method of treating wounds with ozone gas. The treatment is based upon the application of gas to the wound.

U.S. Pat. No. 4,375,812 discloses a method for treating burn injuries with aqueous ozone involving submerging the patients entire body in a bath of aqueous ozone.

SUMMARY OF THE INVENTION

It is an object of the present invention to produce a high concentration ozone solution capable of rapid disinfection and to provide a method and apparatus for applying a high concentration ozone solution to a surface to be disinfected and in particular to a human or animal wound.

This invention discloses an apparatus for disinfecting surfaces and in particular human and animal wounds, although described in the context of a wound surface the scope of the invention covers all types of surfaces, comprising a reservoir for accumulating ozonated water and means to deliver ozonated water from the reservoir to a nozzle having one or more jets for delivering a spray of ozonated water on to the surface to be treated. The nozzle has an encircling shroud and means are provided for withdrawing ozonated gas liberated at the nozzle from around the nozzle. A collection tray is provided which is located under the surface/wound to be treated to receive ozonated water flowing from the treatment region. The base of a catchment tray can contain a number of holes through which used solution is drawn out of the tray by a pump which causes the solution to pass through a catalyst to break down any residual ozone contained in the solution.

BRIEF DESCRIPTION OF THE DRAWINGS

The following is a description of some specific embodiments of the invention, reference being made to the accompanying drawings in which.

DETAILED DESCRIPTION OF THE PREFERRED EMBODIMENTS

Figure 1:
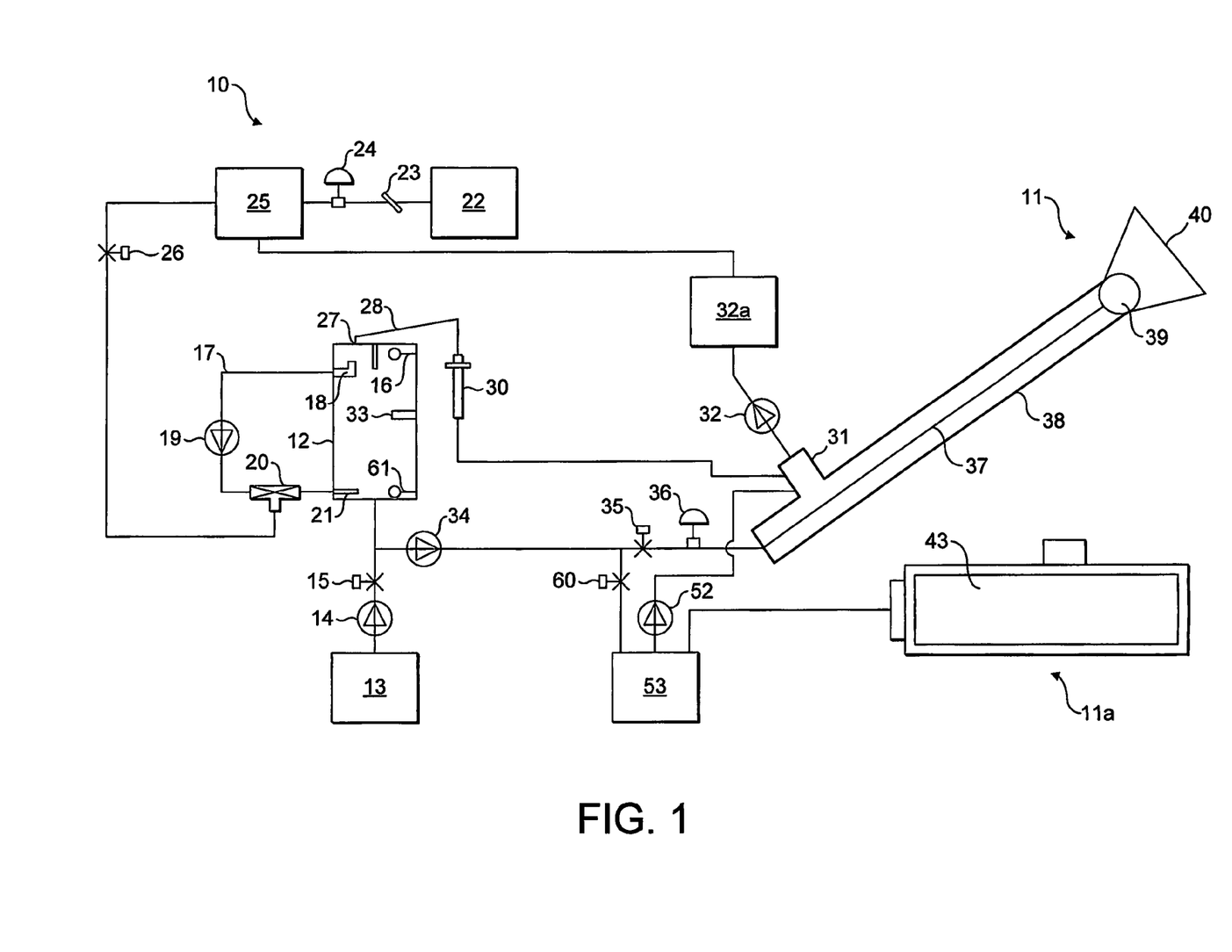
FIG. 1 is a diagrammatic illustration of a system for generating and applying ozonated water to a wound.

Referring firstly to FIG. 1 of the drawings, the apparatus for performing the invention comprises three main components: an apparatus for generating a concentrated aqueous solution of ozone indicated at 10; an apparatus for spraying the ozone solution onto a surface of a limb to be treated indicated at 11; and an apparatus for supporting a limb to be treated and for collecting solution which flows off the treated limb for disposal indicated at 11a. A control system (not shown) is provided for the whole apparatus comprising a programmable logic computer which interfaces with the controllable elements of the apparatus to control the operation of the apparatus.

Figure 2:
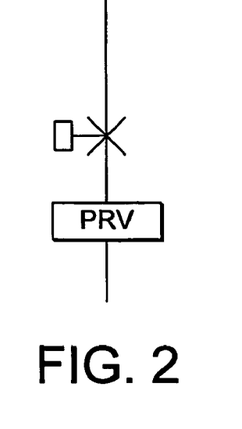
FIG. 2 illustrates a first modification to the system.

The aqueous ozone generator 10 comprises a contactor 12 which is connected to a reservoir of water 13 via a pump 14 and solenoid controlled valve 15. FIG. 2 shows an alternative arrangement in which mains water is supplied via a pressure restriction valve. The pump 14 is activated and solenoid valve 15 is opened to transfer water from the reservoir into the contactor 12 until a sufficient level is reached to activate a water level sensor 16. The sensor activates a relay sending a signal back to the PLC, which turns off a pump 14 and closes a solenoid valve 15.

The contactor has a conduit 17 extending from an upwardly facing inlet 18 adjacent the top of the contactor through a pump 19 and a differential pressure injection 20 (such as a Mazzei injector as disclosed in U.S. Pat. No. 5,863,128) and thence to an outlet 21 into the contactor adjacent the bottom of the contactor. The pump 19 is activated taking in water through the inlet 18, circulating through the differential pressure injector 20 and returning it to the contactor via the nozzle outlet 21. The nozzle serves two functions. Primarily it provides the back pressure required by the differential injector and secondly, it increases the gas/liquid mixing within the contactor.

An oxygen supply 22, preferentially using an oxygen concentrator, supplies dry oxygen through a throttle valve 23 and a pressure regulator 24 to an ozone generator 25. The valve and regulator can be located either before or after the ozone generator. The ozone generator can utilise ultra violet, proton exchange membrane or corona discharge based production methods, but preferentially is an air cooled corona based ozone generator.

The ozone generator is activated and a solenoid valve 26 is opened. Ozone is drawn through the differential pressure injector 20 where it contacts the water. The gas/liquid mixture stream is forced through the outlet nozzle 21 and into the contactor 12. Ozone gas bubbles move up through the contactor and exit at an outlet 27 into a pipe 28.

The pipe 28 is angled downwardly towards the outlet so that any condensation that occurs within the pipe runs back down through the outlet and into the contactor 12.

Any ozone gas which reaches pipe 28 passes through a destruct device 30, where it is broken down into oxygen. A heating element 30a is activated heating ozone destruct unit 30. A temperature sensor 30b is linked back into the programmable logic computer (PLC), which controls the heating process and maintains the destruct unit 30 at a constant temperature between 40 and 80° C., but preferentially 60° C. The destruct 30 is heated, which prevents moisture forming within the destruct itself. The oxygen gas which exits destruct 30 passes into manifold 31. The oxygen gas is drawn from the manifold by a fan 32 and into a secondary ozone destruct device 32a. The oxygen gas exits the secondary ozone destruct device from where it is directed onto the ozone generator 25 referred to earlier where it aids in cooling the unit.

Returning to the ozonation process in the contactor, inlet 18 to the re-circulation system has an upturned end and is shaped to prevent ozone gas bubbles being sucked into the re-circulation system. The aqueous ozone concentration is monitored by a dissolved ozone sensor 33 linked into the PLC. When the dissolved ozone concentration reaches the desired level, set by the operator, the PLC switches off the oxygen concentrator and the ozone generator and closes solenoid controlled valve 26. Pump 19 is switched off and a pump 34 activated for delivering the aqueous solution of ozone to the spray system 11. A solenoid valve 35 is opened and the solution moves along the pipe where the pressure is restricted to between 40 and 100 mbar, but preferentially 70 mbar, by a pressure and flow regulator 36.

The aqueous ozone solution is delivered to one end of an inner conduit 37 of a pair of concentric conduits 37,38. The other end of conduit 37 has a spray head 39 for delivery of multiple jets of aqueous ozone.

The spray head is illustrated in FIGS. 4 to 10 and is designed and constructed so as to produce a series of jets, preferentially in an interlocking fan configuration. The spray system although appearing simple has a number of important features. When high concentration ozone solution is forced through an aperture a pressure differential is created and causes the ozone gas dissolved in the stream to come out of solution into the atmosphere (due to ozone's vapour pressure). The higher the pressure differential the greater the amount of gas liberated to atmosphere. The legal atmospheric limit for ozone is 0.1 ppm, which is very low. Hence the spray head has been developed to use "jet holes" 41 (see FIGS. 7 and 10) that are sufficiently small to use low quantities of solution (facilitating the small size of the unit) and yet have a large enough diameter to prevent an excessively high pressure differential being created that liberates too much ozone gas from the solution. The pressure at which the ozone solution is supplied to the head is also a factor and tests have indicated that a level around 70 mbar is the most suitable. Higher pressures mean more ozone gas is liberated to atmosphere and also causes the jets to be too powerful "drilling" bugs down into the surface of the wound.

Figure 4:
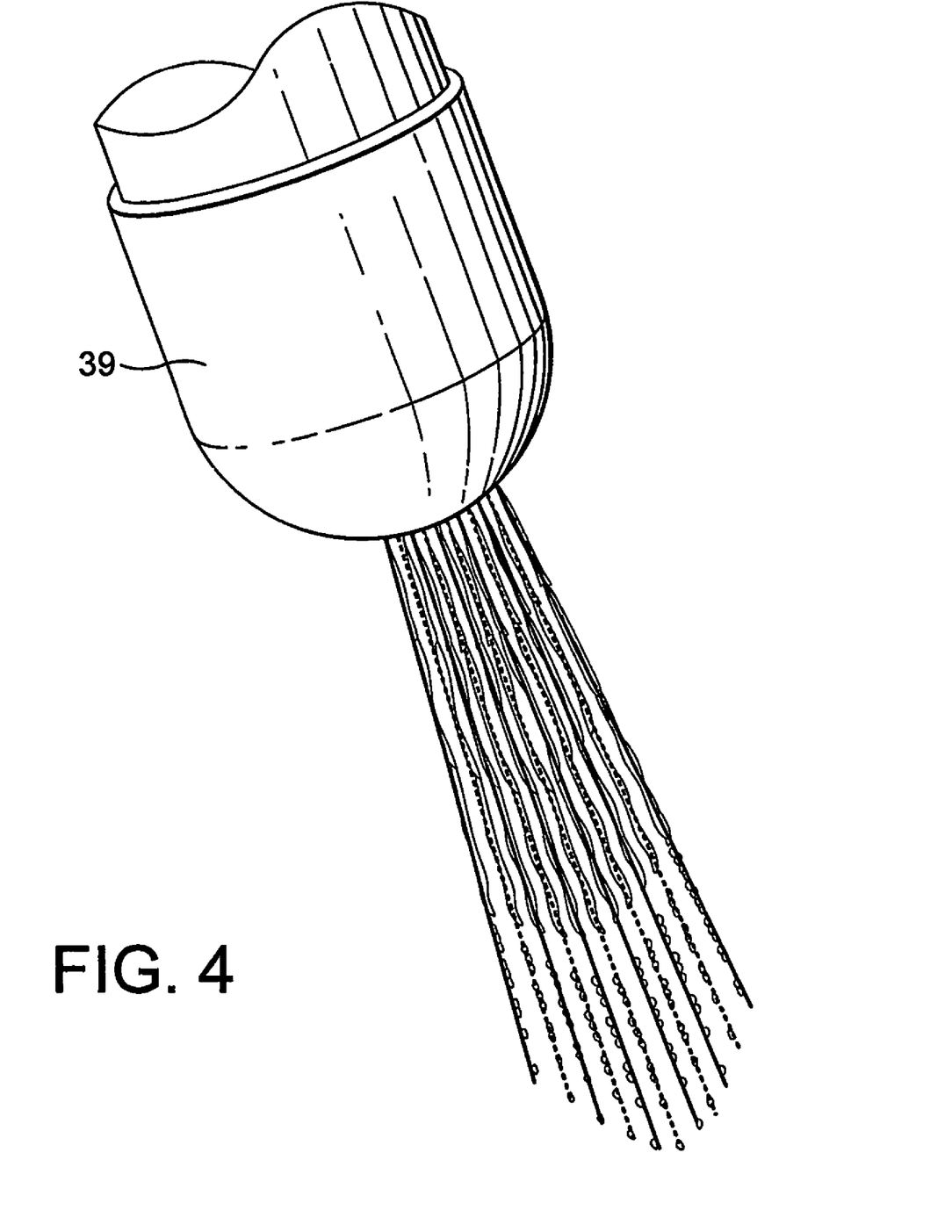
FIGS. 4 to 10 illustrate a spray head for the apparatus.
Figure 5:
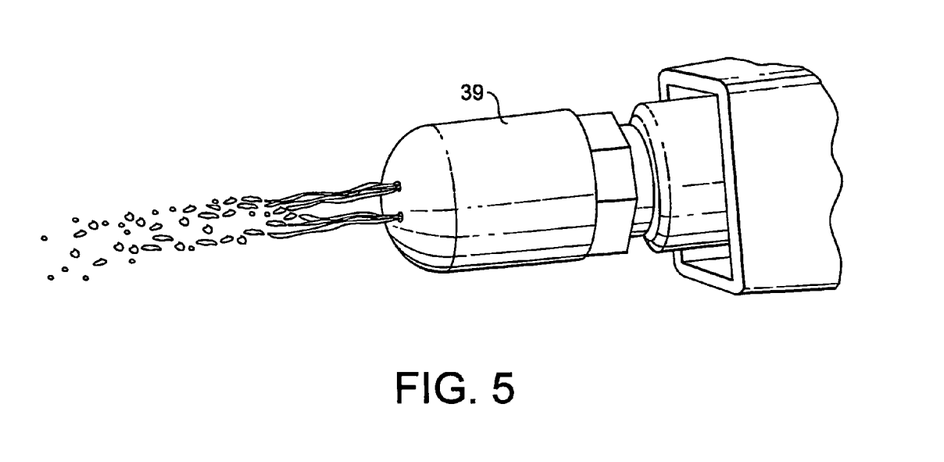
Figure 6:
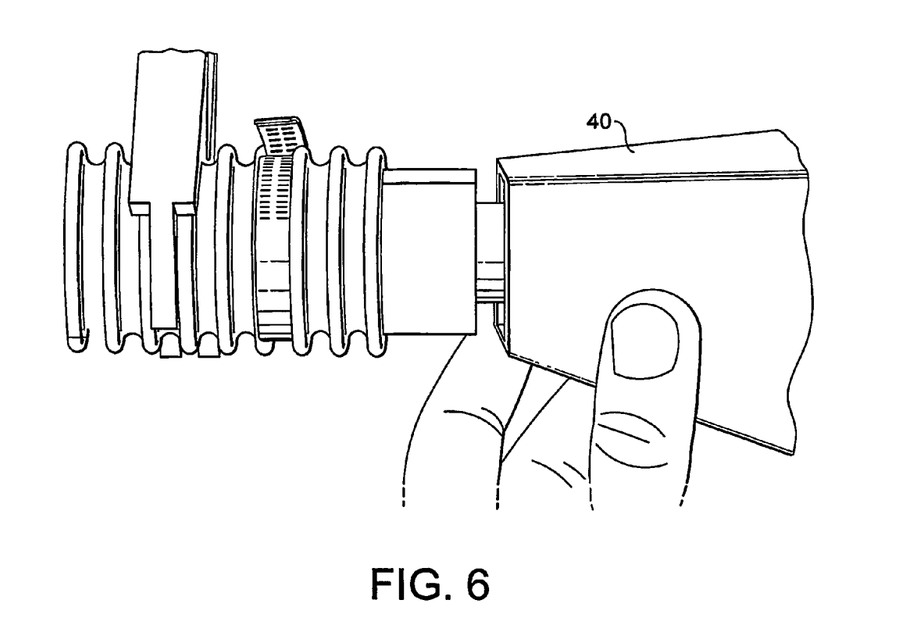

As the solution exits the spray head 39, the pressure drop causes ozone gas to come out of solution. An overlapping arrangement of the jets as can be seen in FIGS. 4 and 5 minimises the surface to volume area of the outer edges of the spray cone, thus reducing the amount of ozone gas that is liberated from the solution. Ozone will rapidly decompose in air and hence the reduced surface to volume ratio is critical in preventing the decomposition of the ozone solution as it is travelling from the spray head to the wounds surface. The jets operate at very low pressures to minimise the amount of ozone gas that escapes from solution and also to ensure that micro-organisms are not driven down into the wound bed. The spray head is located within a head attachment (further referred to as the "cone head") 40, shaped to match the dimensions of the "jet cone" produced by the spray head. The length of the cone head is dependent upon the pressure of the jets, but is preferentially 125 mm. The inside of the cone head is maintained at a negative pressure to the atmosphere by the fan 32 connected to the manifold 31. Any ozone gas released from solution in the spraying process is drawn back through outer conduit 38 into the manifold and subsequently passed through a secondary ozone destruct 32a, where it is decomposed to oxygen.

In use the cone head 40 is positioned over a wound to be decontaminated/healed. The distance from the wound surface to the edge of the cone head is dependent on the pressure of the jets but is preferentially 10 mm.

The patient whose wound is to be disinfected/healed can be bed-ridden or mobile. A collection tray 43 which will be described in greater detail below is placed under the patient's appendage on which the wound is located. The catchment tray contains a jointed support mechanism (not shown) that takes the weight of the patient's appendage during the treatment. The support mechanism can be rigid or flexible, but preferentially comprises of a removable padded concave or convex support, located upon a knuckle joint to facilitate horizontal rotation. This in turn is located on a stem fixed to the collection device by means of a joint 47 that allows the stem to move in an arc in the vertical plane. Preferentially this is a pin joint. The catchment tray has a removable insert 48 that has holes 49 in it to allow the used solution to drain to the base of the tray. This insert 48 will preferentially be a 'Vee' with a series of holes 49 that allow the solution to drain through but retain any large biological material flushed off the wound in the disinfection process. The catchment tray has side flanges 50 upon which the spray head system is mounted.

The spray head 39 is fixed to a mounting and support device (not shown) that securely holds the spray cone in position above the wound. This mounting device can comprise of a wide range of structures to retain the head in its required position, typically either a mechanical or electromagnetic device to provide attachment to a flexi-rigid conduit upon which the spray head is clamped.

The base of the catchment tray 43 contains a number of holes 51 through which the used solution is drawn out of the tray. A pump 52 creates a negative pressure within vessel 53 coupled to the tray (see FIG. 1) causing the liquid in the collection tray to be drawn into the vessel 53. The gas removed from vessel 53 by pump 52 is directed into manifold 31, where it passes through the secondary catalyst 32a. Any residual ozone gas released by the used solution is decomposed here.

The solution is applied to the wound for a period of time determined by the operator and programmed into the PLC at the start of the treatment. Once the required duration has past, the PLC closes valve 35 and continues to operate fan 32 and pump 52 for a defined period of time to clear the catchment tray of solution. During this period valve 60 is opened and the solution within the contactor is pumped into vessel 53, until level switch 61 in the contactor is activated. Pump 34 is turned off and valve 60 is closed. After this period has passed the pump 52 and fan 32 are switched off.

The inlets and outlets of vessels comprise of quick connect couplings to facilitate their ease of removal and attachment. At the end of the treatment, vessel 53 is disconnected and the water contained within it poured straight to drain.

Figure 3:
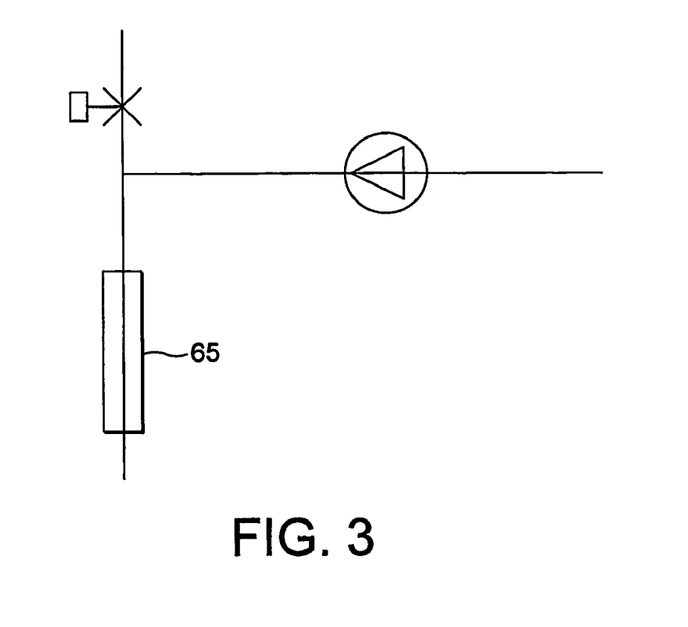
FIG. 3 illustrates a second modification.

FIG. 3 shows an alternative arrangement of the apparatus, whereby vessel 53 is removed and the contents of the catchment tray are pumped directly to drain via a pump. The excess solution remaining in the contactor is pumped directly to drain as opposed to vessel 53. This solution can pass through a carbon filter 65 within the waste pipe line to destroy any ozone that may remain.

The system is described operating with tap water taken from a domestic or commercial supply. The invention does not preclude the use of a filtered or conditioned water supply. Such a water supply will have an effect of speeding up the ozonation process, but is not the preferred water supply of use due to the reduction in portability filtration systems present.

The ability to capture and destroy as much as possible of any aqueous ozone gas released to atmosphere from any aqueous ozone solution is paramount to the successful operation of any unit. The following apparatus is directed to that objective.

Figure 7:
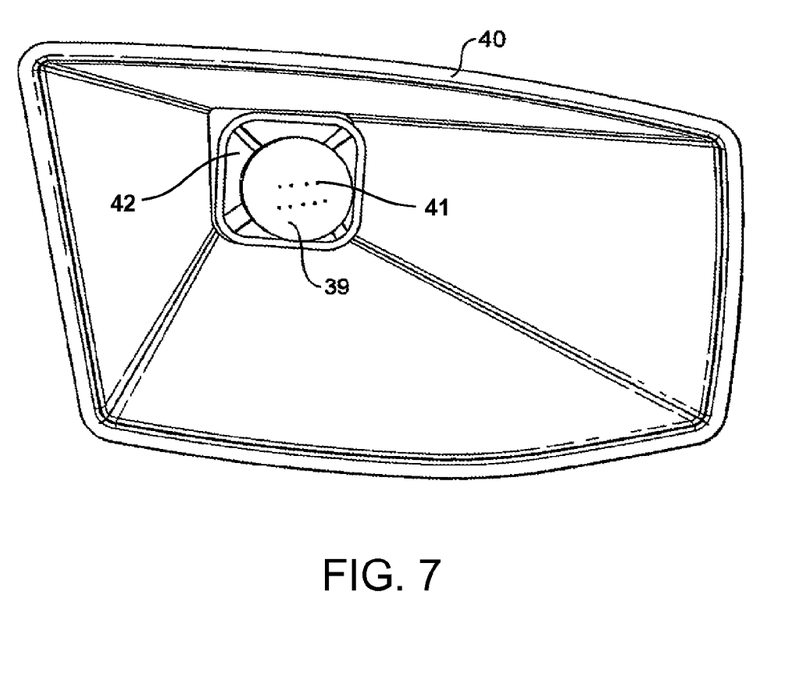
Figure 8:
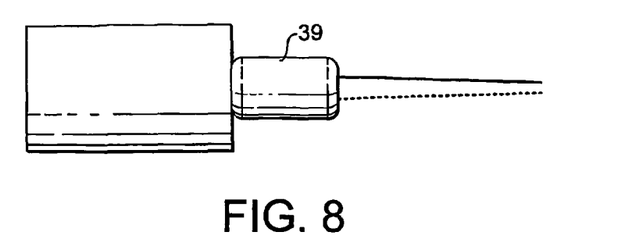
Figure 9:
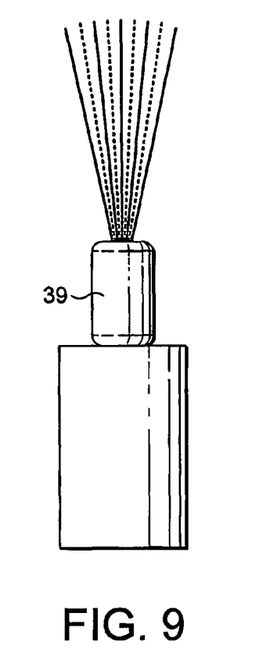
Figure 10:
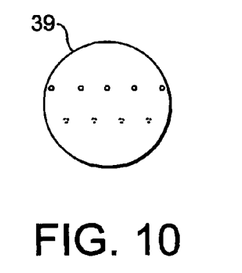

FIG. 7 is an illustration of the nozzle 39 and encircling shroud 40 for the nozzle for applying ozonated water to a patient's wound or other surface; and FIGS. 11 to 15 illustrate the catchment tray supporting the area of the patient's limb or body to be treated and for recovering ozonated water which flows off the area of the patient being treated.

Aqueous ozone is created by dissolving ozone gas into liquid. The saturated vapour pressure of ozone is >760 mmHg at 25 C, which means that ozone will actively diffuse out of the liquid into the atmosphere. Ozone has a legal exposure limit of 0.1 ppm and hence this poses a problem when a high concentration aqueous ozone solution is exposed to the atmosphere (the ozone readily comes out of solution and the concentration in the atmosphere rises above the 0.1 ppm limit).

The rate at which the ozone gas liberates from the liquid is highly dependent on temperature and pressure. The higher the temperature the more ozone comes out of solution and the lower the pressure the more ozone comes out of solution.

The aqueous ozone solution is produced at atmospheric pressure. It is then placed under increased pressure as it is pumped to the spray head. When it is under pressure (i.e. in the pipe from the pump to the spray head) no ozone comes out of solution, because of the fact that it has been put under increased pressure. When it reaches the spray head, it is suddenly exposed to normal atmospheric conditions (i.e. a drop in pressure occurs) and hence a proportion of the ozone contained in the liquid stream is released to atmosphere. There is a pressure differential created across the aperture(s) in the spray head. The size of this pressure differential determines the amount of ozone gas that is released from the liquid as it exits the spray head. The release of ozone gas has two consequences, the first has already been explained, ozone gas is toxic and hence raises the atmospheric concentration above the legal exposure limit. The second is that the concentration of the aqueous ozone fluid drops. The purpose of the system is to apply a high concentration solution to the wound, hence the amount of concentration loss due to ozone gas liberation needs to be minimised.

Experiments were conducted using spray heads with varying sized apertures combined with alternating pressures from the pump. It was found that a 0.5 mm diameter aperture is the most effective size, combined with a liquid pressure of 70 mbar. 0.2 mm diameter apertures produced a pressure differential that was too large and liberated a substantial amount of ozone gas, dropping the solution concentration from 20 ppm down to 12 ppm. A 0.75 mm diameter aperture allowed too much liquid through the head. Too much liquid will cause a wound to macerate and hence would inhibit rather than aid the healing process.

The 0.5 mm diameter aperture still allows a proportion of the ozone gas to escape from the liquid, due to the change in pressure. The concentration drops from 20 ppm to 17 ppm. The ozone gas that escapes to the atmosphere has to be dealt with; otherwise over a period of time the cumulative effect would raise the ozone concentration above 0.1 ppm. To that end the spray head is surrounded by an extraction system (outer conduit 38, shroud 40), so that as the ozone gas is liberated on exiting the spray head it is immediately taken back into the machine through an opening 42 encircling the spray head 39 in the extract air stream.

The use of an extract system dictates the design and shape of the spray pattern exiting the spray head. The implementation of an extract system means that ozone gas is continually being stripped from the surface of the air borne aqueous liquid from the spray head to the wound.

The amount of ozone gas being removed can be limited by reducing the surface to volume ratio of the spray cone. The optimal spray configuration is one that has a very small surface area exposed to the extract air stream, whilst providing a large surface impact area. The spray head has a series of interlocked jets (see FIGS. 4 and 5) that produce a dual fan effect. This may or may not be the most optimal configuration for the spray pattern.

The extract "shroud" 40 is intended to be a consumable item (i.e. it can be quickly replaced between patients).

As explained earlier, ozone gas actively diffuses out of aqueous solution. When aqueous ozone is sprayed on to a wound or other organic surface, a large proportion of the ozone is broken down on the surface. However, the waste run-off liquid still contains ozone, which, as previously described, will actively enter into the atmosphere. The catchment tray has two main "concepts" that allow it to function.

The first of these relates to the catchment tray 43 which is basically a tray that has a solid plastic insert 48, which is angled in an inverted V shape. A series of holes 49 (e.g. four cm apart are drilled along the apex of the V. The insert allows aqueous ozone solution to pass through the holes, but capture any gas released in the gap underneath the insert preventing it from escaping to atmosphere.

The second concept of the catchment tray is a catalyst break down arrangement. A pair of six inch fans 70 are mounted horizontally above the waste liquid collection area 71. Below each fan is a bed 72 of ruthenium pellets or other catalytic material, through which the fans draws air.

Figure 11:
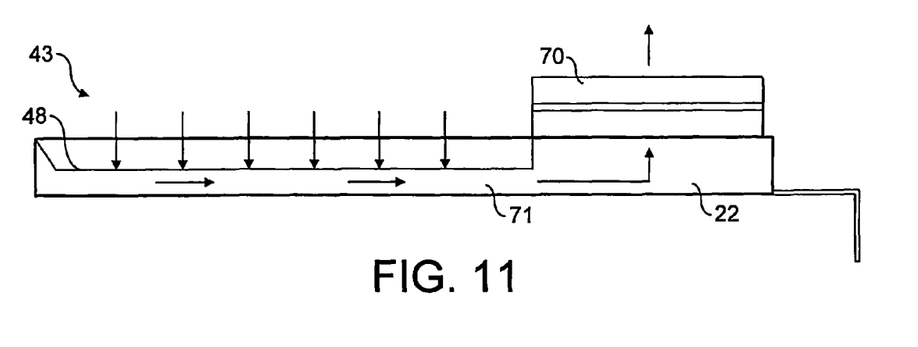
FIGS. 11 to 15 illustrate a catchment tray and limb support for a patient to be treated.
Figure 12:
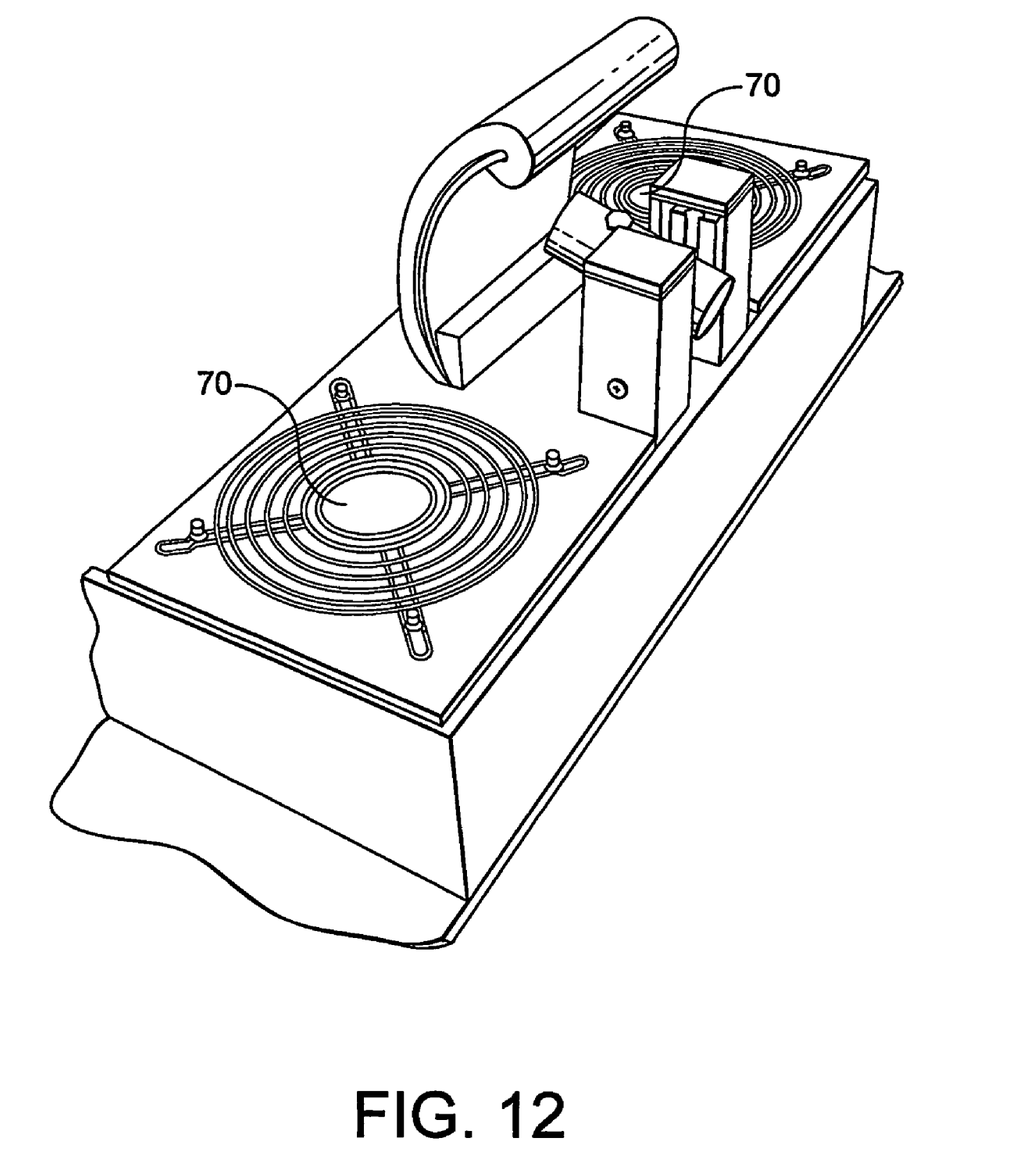
Figure 13:
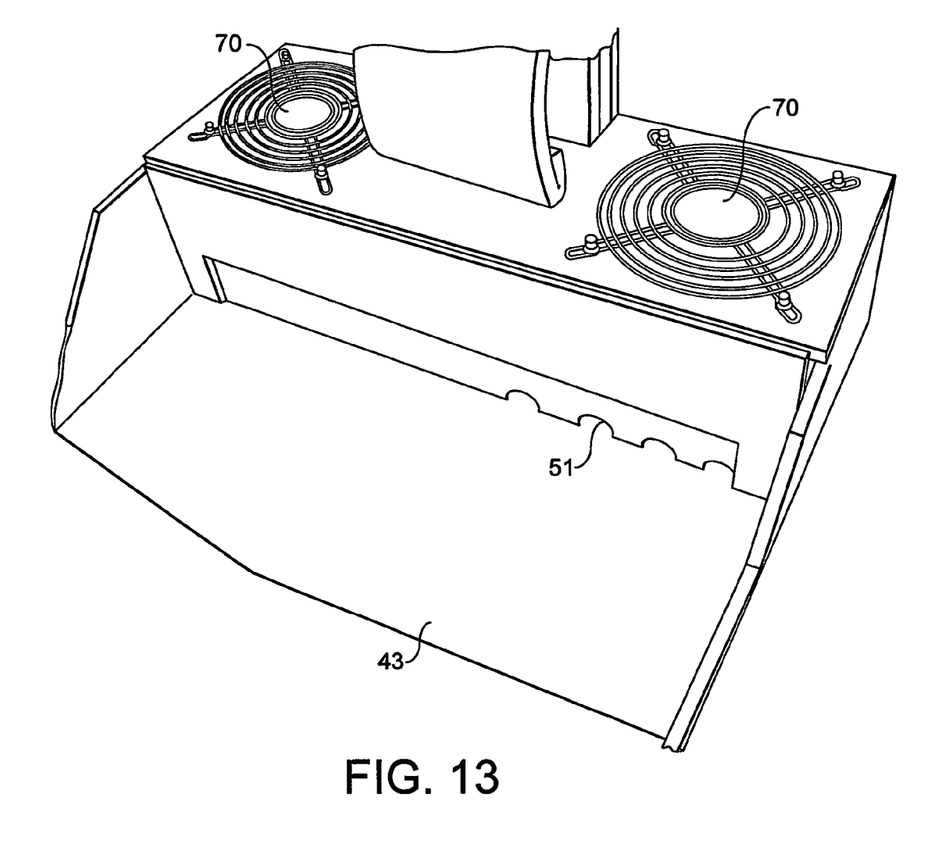
Figure 14:
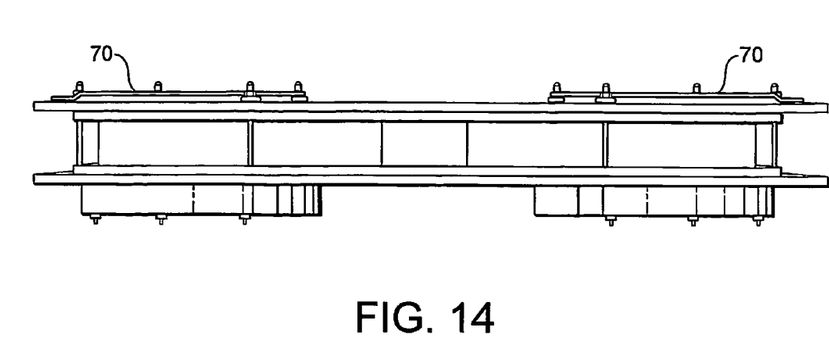
Figure 15:
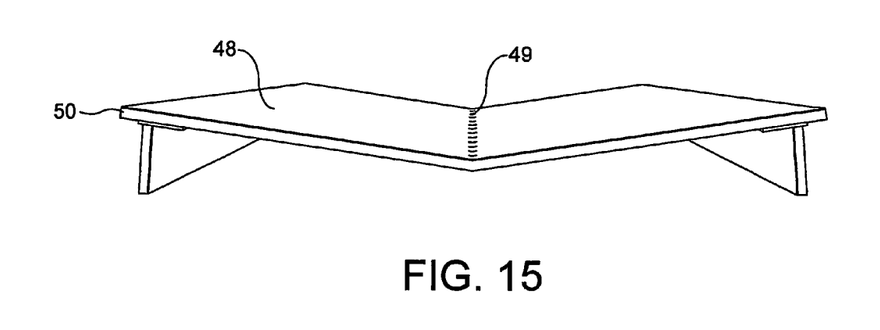

As can be seen in FIG. 11 the fans draws in air (and hence any atmospheric ozone, as ozone is heavier than air) through the holes in the V shaped insert. The air passes over the aqueous ozone liquid drawing off any ozone gas that may be coming out of the solution. This ozone air mix is then drawn through a catalyst, which converts it into oxygen. The oxygen is released into the atmosphere.

Thus the system takes a number of previous systems (ozone generator, oxygen concentrator, differential pressure injector) and combines them in such a way as to produce a portable and highly mobile unit that is able to produce very high aqueous ozone concentrations (>20 ppm).

Previous aqueous ozone based disinfection systems have been based on large less-portable systems or on mobile systems that can only produce low concentration aqueous ozone solutions (5 ppm). The concept of applying ozone to wounds is not novel, however the theories developed based on the inventors research and understanding of biological systems and their modes of interaction with aqueous ozone is novel. The development of an effective system to apply high concentration aqueous ozone to a human (or animal) without endangering the patient through exposure to ozone gas is novel and inventive. The invention incorporates an aqueous ozone delivery system that delivers the high concentration solution to the wound surface whilst minimising the amount of ozone gas released from that solution. The design of the spray configuration, the pressure requirements and the spray head enclosure design are all novel in regard to minimising ozone gas release. The use of an extraction system to remove ozone gas from the wound area is novel, as is the design, which incorporates the aqueous ozone delivery conduit and ozone gas extract into a single pipe system.

The catchment tray also incorporates other important design features. The perforated insert tray is designed to allow aqueous ozone solution to pass through to the bottom of the tray. Ozone gas is heavier than air and hence will remain at the bottom of the tray. The insert 48 functions to trap the ozone gas in the bottom of the tray away from the patient. Waste solution within the tray is removed by a peristaltic pump and fan system, therefore removing the ozone gas as well as the waste solution. The arrangement has been designed so that all sources of ozone gas are extracted back to a single manifold at the input to the systems main fan, which forces the gas through a catalytic destruct. The design of the system is novel and inventive in that a single catalyst is used as a final destruct for gas coming from three individual sources. Further, the catalytically reacted gas is directed to and exhausted over the surface of the ozone generator, which is preferentially an air-cooled (as opposed to water-cooled) generator.

The primary catalytic destruct is novel and inventive. Catalytic destructs are designed to operate with dry gas supplies, as water poisons most catalysts. The design of the system allows the catalyst to destroy wet ozone gas, without damaging the catalyst.

The apparatus allows the user to determine the concentration of the solution that is to be applied to the surface (preferentially ranging from 1-21 ppm). The user is able to select the aqueous ozone concentration required at the start of the cycle. The user is also able to select the duration for which the solution is to be applied to the surface.

The invention claimed is:

1. An apparatus for producing a spray of ozonated water for disinfecting a surface comprising
    a reservoir for water,
    means for supplying ozone to the reservoir water,
    a nozzle having a plurality of jets for spraying ozonated water onto a surface to be treated,
    a supply conduit for delivering the ozonated water from the reservoir to the nozzle,
    a shroud for the nozzle having one end in which the nozzle is fitted and having an enlarged mouth at the other end, the nozzle facing the enlarged mouth of the shroud to deliver said spray of ozonated water from the shroud,
    an outer conduit extending concentrically along said supply conduit from said one end of the shroud, the shroud having an opening into the outer conduit extending around the nozzle, and
    means for creating a negative pressure in the outer conduit away from said one end of the shroud to draw ozone gas liberated from the spray of ozonated water from the shroud through said opening and into the outer conduit to prevent release of ozone gas to atmosphere, wherein the nozzle is mounted on a support structure located at one end of the outer conduit, the support structure comprising a variable position clamping device.

2. An apparatus as claimed in claim 1, wherein the jets are located to produce an overlapping spray pattern.

3. An apparatus as claimed in claim 1, wherein the nozzle comprises a spray head having a number of orifices between 0.2 mm and 1.5 mm in diameter.

4. An apparatus as claimed in claim 3, wherein the diameter of the orifices is 0.5 mm.

5. An apparatus as claimed in claim 1, further comprising a pump arranged to pump the ozonated water to the nozzle at a pressure of between 50 and 100 mbar.

6. An apparatus as claimed in claim 5, wherein the pump is arranged to pump the fluid at a pressure of 70 mbar.

7. An apparatus as claimed in claim 1, wherein the shroud is pyramidal in shape and has an open end to encircle a wound through which the spray is delivered.

8. An apparatus as claimed in claim 7, wherein the dimensions of the shroud are such as to closely contain, yet not interfere with, the fluid spray pattern.

9. An apparatus as claimed in claim 1, wherein the means for creating a negative pressure comprises a suction device connected to the opposite end of the outer conduit than the end where the support structure is located.

10. An apparatus as claimed in claim 1, wherein the reservoir for ozonated water has a circuit extending from an upper level of the reservoir and returning to the reservoir at a lower level, the circuit including
a pump for drawing off liquid at the upper level in the reservoir and returning the liquid at the lower level,
an ozonating station and
means to supply ozone to the ozonating station to be dissolved in the flow of circulating liquid returning to the reservoir to enable the ozone concentration in the water to be raised to a requisite level prior to delivery of ozonated water through the supply conduit to the spray nozzle for application to the surface to be treated.

11. An apparatus as claimed in claim 10, wherein the circuit has an inlet in the reservoir which is upwardly open to minimise entry of bubbles of ozone into the inlet.

12. An apparatus as claimed in claim 10, wherein the ozonating station comprises a venturi through which the water in the circuit passes and to the constriction of which the ozone gas is supplied to be entrained in the water flow.

13. An apparatus as claimed in claim 10, wherein the means for supplying ozone gas into the water within the circuit is a differential pressure injector.

14. An apparatus as claimed in claim 1, wherein the reservoir has means for measuring the dissolved ozone concentration and/or the oxidation reduction potential of the fluid; and means for applying said fluid.

15. An apparatus as claimed in claim 1, wherein the reservoir has a common orifice for delivery of water to the reservoir and supply of ozonated water from the reservoir.

16. An apparatus as claimed in claim 1, wherein any undissolved gas in the reservoir is captured and passed through a destruct device.

17. An apparatus as claimed in claim 16, wherein the destruct device comprises:

a) a gas decomposition unit for breaking down ozone gas;

b) a heating element c) and a temperature sensor.

18. An apparatus as claimed in claim 17, wherein the destruct unit comprises a manganese dioxide catalyst for breaking down the ozone gas.

19. An apparatus as claimed in claim 17, wherein the gas decomposition unit is connected to the reservoir by a tube angled to the horizontal to allow water resulting from the condensation ozone to flow back to the reservoir.

20. An apparatus as claimed in claim 17, wherein the heating element and the temperature sensor keep the gas decomposition unit at a temperature of between 40 and 80° C.

21. An apparatus as claimed in claim 17, wherein the decomposed gas is directed through a secondary destruct unit.

22. An apparatus as claimed claim 21, wherein the secondary destruct unit is an activated carbon catalyst.

23. An apparatus as claimed in claim 17, wherein means are provided to apply negative pressure around the region where the reaction fluid is sprayed onto a surface.

24. An apparatus as claimed in claim 17, wherein a device is provided for supporting a patient's appendage to be treated and collecting fluid sprayed onto a wound on the appendage, the reaction fluid is sprayed onto a wound and is subsequently collected in a device, onto or into which the patients' appendage is placed.

25. An apparatus as claimed in claim 1, wherein the equipment is portable.

26. An apparatus as claimed in claim 1, wherein the ozone is dissolved within the water when the water is in the supply conduit.

27. An apparatus as claimed in claim 1, wherein the ozonated water has an aqueous ozone concentration greater than 20 ppm.

28. An apparatus as claimed in claim 1, further comprising means for removing ozone from the reservoir, the removed ozone corresponding to ozone that has not dissolved in the water.

29. An apparatus for producing a spray of ozonated water for disinfecting a surface comprising a reservoir for water, a nozzle for spraying ozonated water onto a surface to be treated, a conduit for delivering water from the reservoir to the nozzle and means for supplying ozone to the water to be delivered as a spray of ozonated water from the nozzle;

wherein the nozzle has one or more jets for delivering the spray of ozonated water, a shroud encircles the nozzle and extends from the nozzle along the conduit to contain ozonated gas liberated at the nozzle and means are provided for creating a negative pressure at the end of the shroud remote from the nozzle to extract ozone gas liberated at the nozzle, wherein the nozzle comprises a spray head having a number of orifices to produce jets of ozonated water from said supply, and wherein the nozzle is located at an end of a supply conduit, and the shroud comprises an outer conduit encircling the supply conduit and having an enlarged head encircling the nozzle at one end and a suction device is connected to the outer conduit at the other end thereof to extract ozone gas from within the head through the outer conduit away from the nozzle, wherein the spray head is mounted on a support structure located at said one end of the outer conduit, and wherein the other end of the conduit is connected to the suction device, wherein the support structure consists of a switchable electromagnetic base and a variable position clamping device.

30. An apparatus for producing a-spray of ozonated water for disinfecting a surface comprising:
a reservoir for water;
means for supplying ozone to the water in the reservoir;
a nozzle for spraying ozonated water onto a surface to be treated;
a first conduit for delivering the ozonated water from the reservoir to the nozzle;
a shroud having an interior surface that bounds a cavity and that outwardly flares along a longitudinal axis from a constricted first end to an enlarged second end, the first end of the shroud encircling the outlet of the nozzle, the nozzle being positioned so that ozonated water sprayed from the outlet of the nozzle passes out of the cavity of the shroud through the enlarged second end; and
a second conduit encircling the first conduit and coupled to the shroud, an opening around the nozzle from the shroud into the second conduit and means connected to the second conduit for applying a negative pressure to the cavity of the shroud so that ozone gas liberated at the outlet of the nozzle within the cavity of the shroud is extracted out of the cavity of the shroud through the second conduit,
wherein the nozzle is mounted on a support structure located at one end of the second conduit, the support structure comprising a variable position clamping device.

31. An apparatus as claimed in claim 30, wherein the ozone is dissolved within the water when the water is in the first conduit.

* * * * *

UNITED STATES PATENT AND TRADEMARK OFFICE
CERTIFICATE OF CORRECTION

PATENT NO. : 7,967,800 B2
APPLICATION NO. : 10/557862
DATED : June 28, 2011
INVENTOR(S) : John G. Chewins It is certified that error appears in the above-identified patent and that said Letters Patent is hereby corrected as shown below:

Drawings
Sheet 6, replace Figure 11 with the figure depicted below, wherein the reference number "22" has been changed to --72--

FIG. 11

Column 1
Line 60, change "conclude" to --concluded--
Line 63, change "anerobes as visible villans" to --anaerobes as invisible villains--

Column 4
Line 54, change "patients" to --patient's--

Column 6
Line 20, change "destruct 30" to --destruct device 30--
Line 21, change "destruct 30" to --destruct device 30--

Column 9
Line 50, change "to atmosphere" to --to the atmosphere--
Line 55, change "draws" to --draw--

Signed and Sealed this
Seventh Day of February, 2012

David J. Kappos
*Director of the United States Patent and Trademark Office*

Column 10
Line 6, change "inventors" to --inventor's--
Line 51, change "comprising" to --comprising:--

Column 11
Line 33, change "including" to --including:--

Column 12
Line 38, change "comprising" to --comprising:--